(12) United States Patent
Kawata et al.

(10) Patent No.: US 9,877,689 B2
(45) Date of Patent: Jan. 30, 2018

(54) DETECTION DEVICE AND DATA PROCESSING METHOD

(71) Applicant: KABUSHIKI KAISHA TOSHIBA, Tokyo (JP)

(72) Inventors: Go Kawata, Tochigi (JP); Shunsuke Kimura, Kanagawa (JP); Rei Hasegawa, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 15/262,398

(22) Filed: Sep. 12, 2016

(65) Prior Publication Data

US 2017/0086762 A1    Mar. 30, 2017

(30) Foreign Application Priority Data

Sep. 30, 2015   (JP) ................. 2015-194049

(51) Int. Cl.
| | |
|---|---|
| G01T 1/20 | (2006.01) |
| A61B 6/00 | (2006.01) |
| A61B 6/03 | (2006.01) |
| G01T 1/18 | (2006.01) |
| G01T 1/17 | (2006.01) |
| G01T 1/29 | (2006.01) |

(52) U.S. Cl.
CPC ............ *A61B 6/4241* (2013.01); *A61B 6/032* (2013.01); *A61B 6/4233* (2013.01); *G01T 1/17* (2013.01); *G01T 1/18* (2013.01); *G01T 1/20* (2013.01); *G01T 1/2985* (2013.01)

(58) Field of Classification Search
CPC .................................................. G01T 1/2985
See application file for complete search history.

(56) References Cited

U.S. PATENT DOCUMENTS

| | | |
|---|---|---|
| 6,355,921 B1 | 3/2002 | Staton et al. |
| 7,260,174 B2 | 8/2007 | Hoffman et al. |
| 7,512,210 B2 | 3/2009 | Possin et al. |
| 2005/0069337 A1 | 3/2005 | Suzumi et al. |
| 2008/0240341 A1 | 10/2008 | Possin et al. |

(Continued)

FOREIGN PATENT DOCUMENTS

| | | |
|---|---|---|
| JP | 2000-356594 | 12/2000 |
| JP | 2005-107237 | 4/2005 |

(Continued)

OTHER PUBLICATIONS

Chu et al., "Combination of current-integrating/photon-counting detector modules for spectral CT," 2013 Physics in Medicine and Biology, vol. 58, pp. 7009-7024.*

(Continued)

*Primary Examiner* — Kiho Kim
(74) *Attorney, Agent, or Firm* — Finnegan, Henderson, Farabow, Garrett & Dunner, L.L.P.

(57) ABSTRACT

According to an embodiment, a detection device includes a plurality of first detectors and a plurality of second detectors. The plurality of first detectors are arranged on a two-dimensional plane. Each first detector is configured to detect photons in a photon-counting manner. The plurality of second detectors are arranged on the two-dimensional plane. Each second detector is configured to detect photons in a charge-integrating manner.

9 Claims, 6 Drawing Sheets

(56) References Cited

U.S. PATENT DOCUMENTS

2010/0102242 A1* 4/2010 Burr .................... G01T 1/20
 250/370.11
2015/0223766 A1* 8/2015 Besson ................ G01T 1/2985
 378/5

FOREIGN PATENT DOCUMENTS

| JP | 2006-284472 | 10/2006 |
| JP | 2009-18154 | 1/2009 |
| JP | 2015-31683 | 2/2015 |

OTHER PUBLICATIONS

Fink et al., "Comparison of pixelated CdZnTe, CdTe and Si sensors with the simultaneously counting and integrating CIX chip," 2009, IEEE Transaction on Nuclear Science, vol. 56, No. 6, pp. 3819-3827.*

* cited by examiner

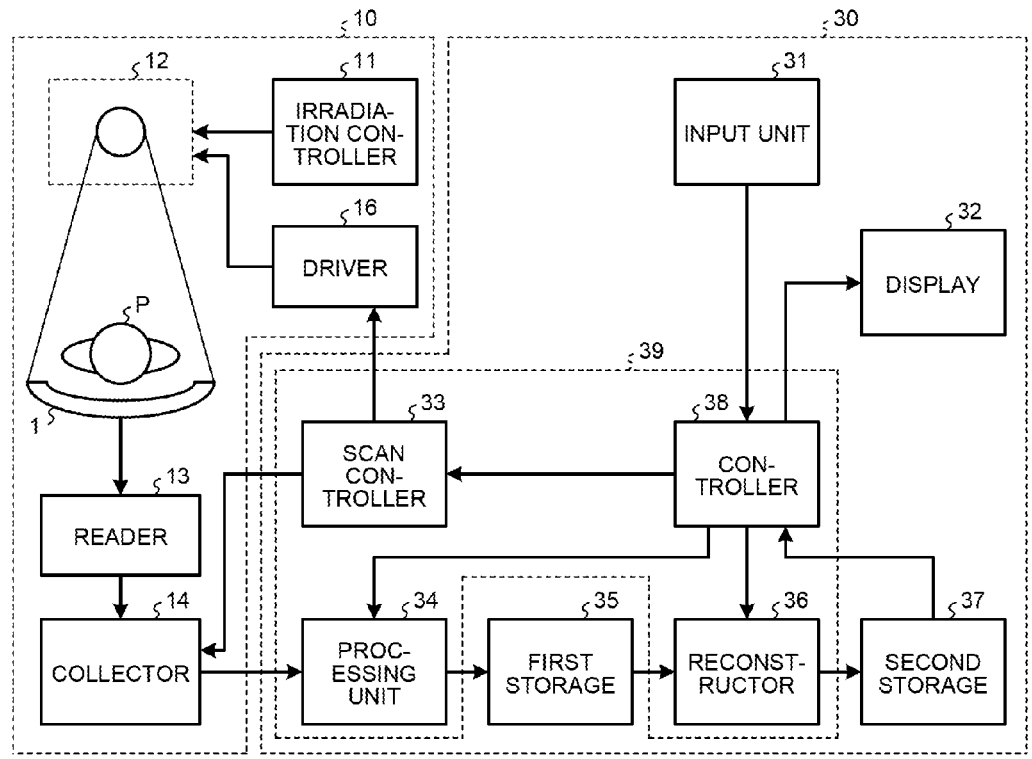
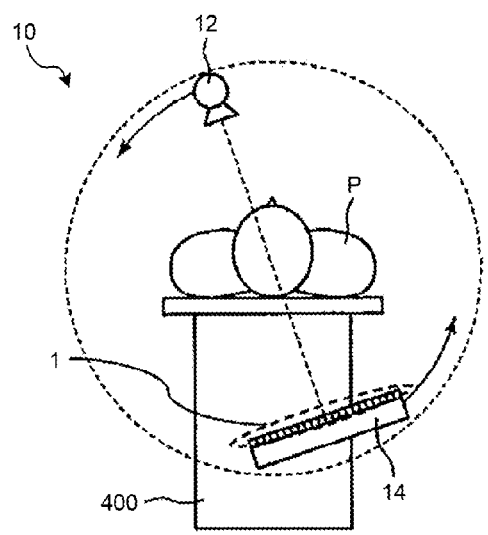

DETECTION DEVICE AND DATA PROCESSING METHOD

CROSS-REFERENCE TO RELATED APPLICATION

This application is based upon and claims the benefit of priority from Japanese Patent Application No. 2015-194049, filed on Sep. 30, 2015; the entire contents of which are incorporated herein by reference.

FIELD

An embodiment described herein relates generally to a detection device and a data processing method.

BACKGROUND

Photon-counting computed tomography (CT) apparatuses are known that are CT apparatuses employing photon-counting detectors measuring x-rays as photons. An indirect conversion photon-counting detector includes a combination of a scintillator and a photo-detector. The scintillator converts radiation passing through a subject into scintillation light (photons) in proportion to energy of the radiation. Photons emitted by the scintillator enter the photo-detector and a pulse signal is obtained that has a pulse height in proportion to the energy of the radiation. The energy of the radiation entering the photon-counting detector can be measured by analyzing the waveform of the pulse signal output from the photon-counting detector.

The photon-counting detector is superior in detecting photons when an amount of radiation is small. An increase in the amount of radiation causes the photon-counting detector to output a single signal instead of a plurality of pulse signals because the number of radiation photons is counted small due to pulse-pileup of the photon-counting detector. This miss counting, thus, increases the difference between the number of radiation photons entering the photon-counting detector and the number of photons actually detected by the photon-counting detector.

As a radiation detection device included in the CT apparatus, a charge-integrating (energy-integrating) detector is also used. An indirect conversion charge-integrating detector outputs the total amount of the received photons as an electrical signal. Charges generated in the detector are accumulated for a certain time in a capacitor connected to the charge-integrating detector.

The charge-integrating detector is superior in detecting photons when an amount of radiation is large. Unlike the photon-counting detector, the charge-integrating detector accurately detects photons even if the amount of radiation increases. Instead, a signal/noise (S/N) ratio of the electrical signal deteriorates when the amount of radiation is small.

A radiation detection device is desired that can complement shortcomings in respective performances of the photon-counting detector and the charge-integrating detector.

A method is available that performs switching in such a manner that the photon-counting detector functions when an amount of radiation entering the radiation detection device is small while the charge-integrating detector functions when the amount of radiation entering the radiation detection device is large. For switching the photon-counting detector and the charge-integrating detector, it is necessary to switch voltages applied to photo diodes included in the respective photon-counting detector and charge-integrating detector. The radiation detection device fails to detect photons during the switching of the photon-counting detector and the charge-integrating detector. As a result, detection efficiency of photons is reduced.

The embodiment aims to increase the detection efficiency of photons without needing to switch the photon-counting detector and the charge-integrating detector.

BRIEF DESCRIPTION OF THE DRAWINGS

FIG. 1 is a schematic diagram illustrating a computed tomography (CT) apparatus and an image diagnosis apparatus;

FIG. 2 is a schematic diagram illustrating the CT apparatus;

DETAILED DESCRIPTION

Figure 3:
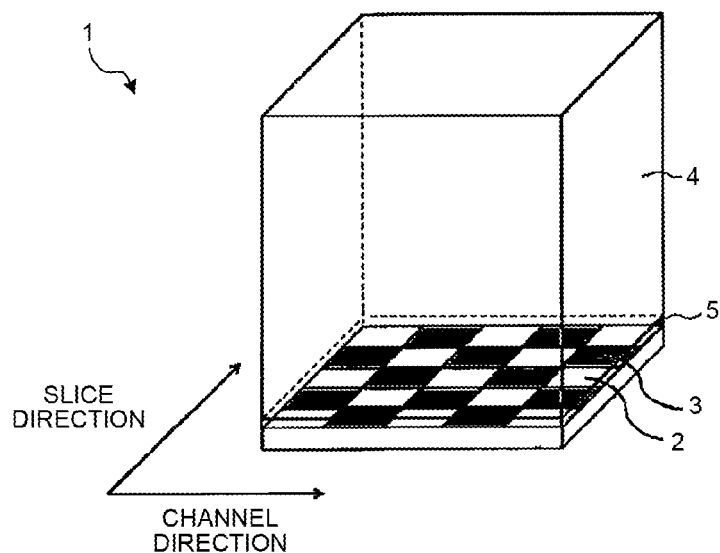
FIG. 3 is a schematic diagram illustrating a detection device in an embodiment.

According to an embodiment, a detection device includes a plurality of first detectors and a plurality of second detectors. The plurality of first detectors are arranged on a two-dimensional plane. Each first detector is configured to detect photons in a photon-counting manner. The plurality of second detectors are arranged on the two-dimensional plane. Each second detector is configured to detect photons in a charge-integrating manner.

The following describes an embodiment with reference to the accompanying drawings. The same components are labeled with the same numerals. The drawings are schematic and conceptual. It is, thus, noted that relation between thicknesses and widths of respective portions and proportions among portions may differ from those of the actual ones, for example. The dimensions and the proportions may be illustrated differently among drawings even for identical portions.

FIG. 1 illustrates a computed tomography (CT) apparatus 10 and an image diagnosis apparatus 30 connected to the CT apparatus 10. In FIG. 1, a subject P is irradiated with x-rays generated by an x-ray generator 12. X-rays passing through the subject P are detected by a detection device (light detection device) 1. The x-ray generator 12 is controlled by an irradiation controller 11. The irradiation controller 11 adjusts an amount of x-rays with which the subject P is irradiated by changing a voltage and a current supplied to the x-ray generator 12. The x-ray generator 12 and the detection device 1 rotate on a circular path around the subject P as the center. The rotational movements of the x-ray generator 12 and the detection device 1 are driven by a driver 16. The outputs of the detection device 1 are transmitted to a reader 13, collected by an collector 14, and thereafter sent to the image diagnosis apparatus 30.

The image diagnosis apparatus 30 reconstructs an x-ray CT image using information acquired by the CT apparatus 10. The image diagnosis apparatus 30 includes an input unit 31, a display 32, a first storage 35, a second storage 37, and a main controller 39.

The main controller 39 includes a scan controller 33, a processing unit 34, the first storage 35, a reconstructor 36, and a controller 38.

Processing functions in the main controller 39 are stored in the storage (e.g., the first storage 35 or the second storage 37) in a form of computer executable programs. The main controller 39 is a processor that reads programs from the storage and executes them to achieve the functions corresponding to the respective programs.

After having read the programs, the main controller 39 has the functions illustrated in the main controller 39 illustrated in FIG. 1. The following description is made on the basis of that the main controller 39 implements the scan controller 33, the processing unit 34, the first storage 35, the reconstructor 36, and the controller 38.

The main controller 39 may be structured by a combination of a plurality of independent processors that achieve the respective functions. In this case, each processor executes the corresponding program to achieve the corresponding function. The functions may be structured as programs and a single processing circuit may execute the programs. A specific function may be implemented by a dedicated independent program execution circuit.

In the embodiment, the term "processor" means a central processing unit (CPU), a graphical processing unit (GPU), an application specific integrated circuit (ASIC), or a circuit of a programmable logic device such as a simple programmable logic device (SPLD), a complex programmable logic device (CPLD), or a field programmable gate array (FPGA). The processor reads a program stored in the storage and executes the program to achieve the function. The program may be directly built in the circuit of the processor instead of being stored in the storage. In this case, the processor reads the program built in the circuit and executes the program to achieve the function.

The processing unit 34 performs various types of processing on signals transmitted from the collector 14 to produce projection data.

The first storage 35 stores therein the projection data produced by the processing unit 34. The projection data is used for reconstructing x-ray CT image data.

The reconstructor 36 reconstructs the x-ray CT image data using the projection data stored in the first storage 35. The reconstructor 36 performs various types of image processing on the x-ray CT image data to produce the x-ray CT image data. The projection data produced by the processing unit 34 includes information about intensity of x-rays attenuated after passing through the subject P. The reconstructor 36 reconstructs the x-ray CT image data using the information about the intensity of x-rays. The reconstructor 36 produces a plurality of pieces of x-ray CT image data that are differently colored from one another in accordance with the intensity information.

The second storage 37 stores therein the x-ray CT image data reconstructed by the reconstructor 36. The x-ray CT image data stored in the second storage 37 is displayed on the display 32 under the control of the controller 38.

The controller 38 controls the whole of the CT apparatus 10. The controller 38 controls the scan controller 33 so as to control the CT scan operation performed by the CT apparatus 10. The controller 38 controls the processing unit 34 and the reconstructor 36 so as to produce the projection data and reconstruct the x-ray CT image data. The controller 38 performs control such that the various types of image data stored in the second storage 37 are displayed on the display 32.

The scan controller 33 controls the irradiation controller 11, the driver 16, and the collector 14 under the control of the controller 38. The scan controller 33 controls the irradiation controller 11 on the basis of the information about an amount of x-rays input via the input unit 31. The scan controller 33 controls the driver 16 such that the driver 16 rotates the x-ray generator 12 and the detection device 1 when the x-ray generator 12 irradiates the subject P with x-rays. The scan controller 33 performs control such that the output of the detection device 1 acquired by the collector 14 is transmitted to the processing unit 34.

The input unit 31 transfers, to the controller 38, various instructions and information about various settings that are input by an operator operating a mouse or a keyboard, for example. The input unit 31 receives, from the operator, imaging conditions of the x-ray CT image data, reconstruction conditions when the x-ray CT image data is reconstructed, and image processing conditions for the x-ray CT image data.

The display 32, which is a monitor that the operator refers to, displays the x-ray CT image data under the control of the controller 38. The display 32 displays the various instructions input by the operator via the input unit 31.

FIG. 2 is a schematic diagram illustrating the CT apparatus 10 including the detection device 1. The CT apparatus 10 includes the x-ray generator 12, the detection device 1, the collector 14, and a couch 400. The subject P lies down on the couch 400.

The detection device 1 detects x-ray photons passing through the object P while rotating around the subject P. A rotation direction of the detection device 1 is defined as a channel direction and the direction orthogonal to the channel direction is defined as a slice direction.

FIG. 3 illustrates the detection device 1. The detection device 1 includes a plurality of photon-counting detectors (first detectors) 2, a plurality of charge-integrating detectors (second detectors) 3, an adhesive layer 5, and a scintillator 4. The photon-counting detectors 2 and the charge-integrating detectors 3 are alternately arranged in the channel direction and the slice direction. The photon-counting detectors 2 and the charge-integrating detectors 3 may be alternately arranged in any one of the channel direction and the slice direction. Each area of the photon-counting detectors 2 and each area of the charge-integrating detectors 3 may differ from each other.

The scintillator 4 is disposed on the photon-counting detectors 2 and the charge-integrating detectors 3. The scintillator 4 converts radiation photons passing through the subject P into scintillation photons in proportional to the energy of the radiation photon passing through the subject P. The radiation photons passing through the subject P are converted by the scintillator 4 into scintillation light. The photon-counting detectors 2 and the charge-integrating detectors 3 detect the scintillation light. The scintillator 4 is fixed on the photon-counting detectors 2 and the charge-integrating detectors 3 with the adhesive layer 5. The scintillator 4 may be individually disposed on each of the photon-counting detectors 2 and the charge-integrating detectors 3.

Examples of a material of the scintillator 4 include thallium doped cesium iodide (CsI(Tl)), thallium doped sodium iodide (NaI(Tl)), and lutetium-yttrium oxyorthosilicate (LYSO)(Lu$_2$(1−x)Y$_2$x(SiO$_4$)O). In the composition formula of LYSO, x satisfies a relation of 0.001<x<0.5. The adhesive layer 5 allows scintillation light from the scintillator to pass through. An example of a material of the adhesive layer 5 is an epoxy material.

Figure 4:
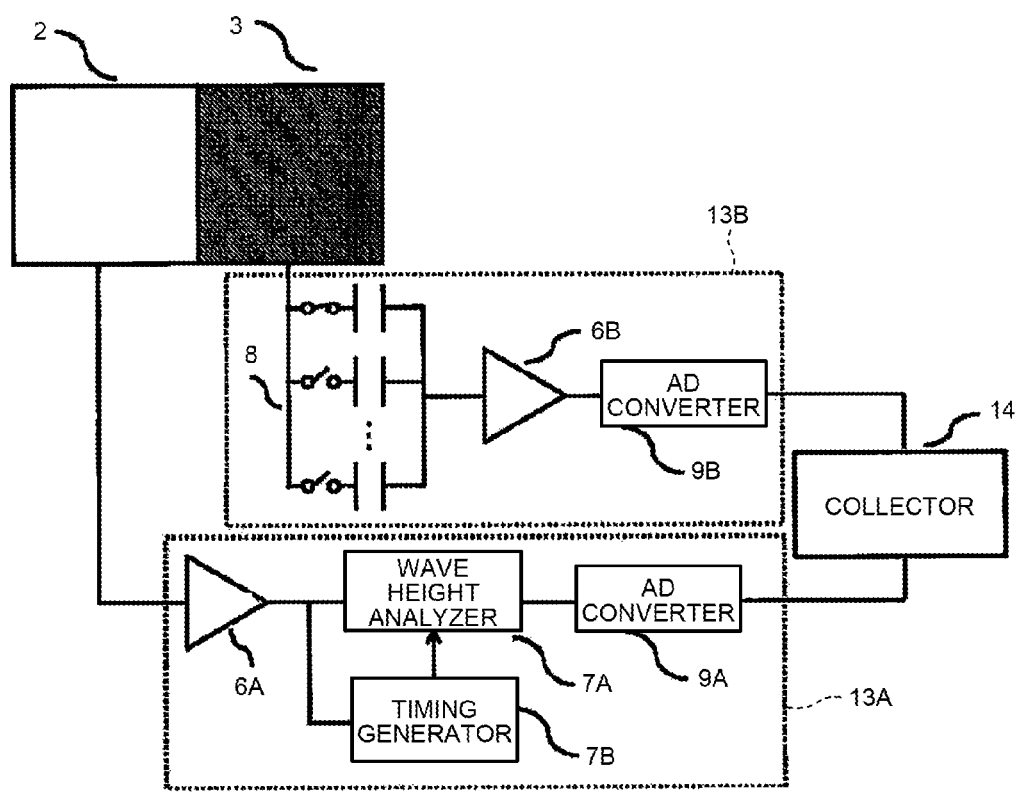
FIG. 4 is a schematic diagram illustrating the structures of readers connected to a photon-counting detector and a charge-integrating detector.

FIG. 4 illustrates structures of a reader 13A connected to the photon-counting detector 2 and a reader 13B connected to the charge-integrating detector 3. For the readers 13A and 13B, an application specific integrated circuit (ASIC) is used, for example. The reader 13A connected to the photon-counting detector 2 includes an amplifier 6A, a pulse height analyzer 7A, a timing generator 7B, and an analog-to-digital (AD) converter 9A. The reader 13A is connected to the collector 14. The reader 13B connected to the charge-integrating detector 3 includes a capacitor (capacitance) 8, an amplifier 6B, and an AD converter 9B. The reader 13B is connected to the collector 14. The pulse height analyzer 7A, the timing generator 7B, and the collector 14 may be operated by a single control device (circuit). The control device detects an electrical signal output from the photon-counting detector 2. The photon-counting detector 2 outputs the electrical signal having a pulse height in proportional to the energy of radiation photons to the reader 13A. The electrical signal is a pulse signal. The pulse signal is amplified by the amplifier 6A and analyzed by the pulse height analyzer 7A. The timing generator 7B notifies the pulse height analyzer 7A of the transmission of the pulse signal. The pulse signal is read by the pulse height analyzer 7A, converted into a digital signal by the AD converter 9A, and acquired by the collector 14. The charge-integrating detector 3 outputs an electrical signal corresponding to the energy of radiation photons to the reader 13B. The electrical signal is send to the capacitor 8, in which the electrical signal is accumulated for a certain time as charges. The charges accumulated in the capacitor 8 are output as an electrical signal. The electrical signal is converted into a digital signal by the AD converter 9B and acquired by the collector 14.

Figure 5:
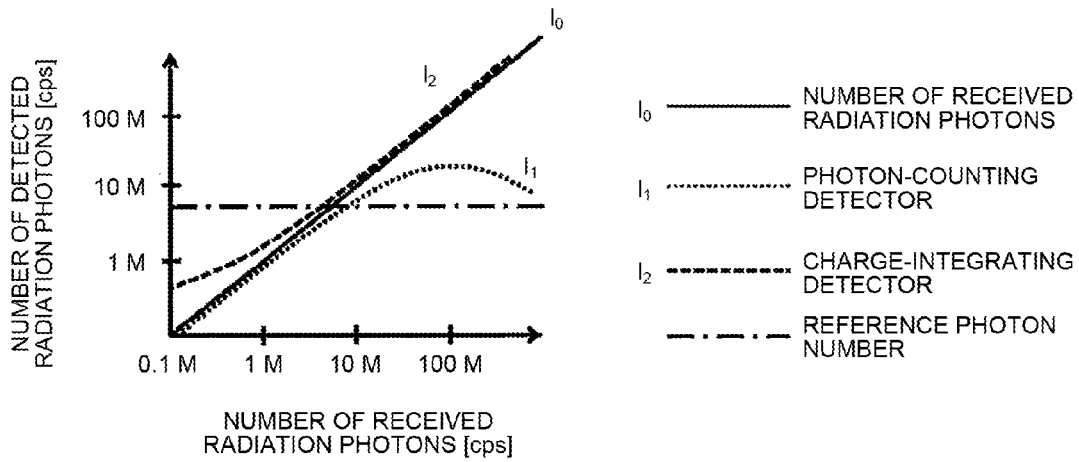
FIG. 5 is a schematic diagram illustrating a relation between the number of received photons and the number of detected photons in relation to the photon-counting detector and the charge-integrating detector.

FIG. 5 illustrates a relation between the number of received radiation photons and detected radiation photons for each of the photon-counting detector 2 and the charge-integrating detector 3. The abscissa axis represents the number of radiation photons per second received by the photon-counting detector 2 or the charge-integrating detector 3. The ordinate axis represents the number of photons per second detected by the photon-counting detector 2 or the charge-integrating detector 3. The abscissa and the ordinate axes represent common logarithm of the respective numbers. The number of received radiation photons and the number of detected photons are represented in a unit of counts per second (cps). The number of received radiation photons is obtained when the CT apparatus 10 is calibrated. With an increase in value of a current applied to the x-ray generator 12, the number of emitted radiation photons is increased. When the value of the current applied to the x-ray generator 12 is small, that is, the number of radiation photons is small, the photon-counting detector 2 accurately detects photons. Let the ordinate represent the value of the current applied to the x-ray generator and the abscissa represent the number of photons per second detected by the photon-counting detector 2. The following Equation (1) holds in relation to x (A), which is the value of the current applied to the x-ray generator 12 when the number of radiation photons is small, and y (cps), which is the number of photons detected by the photon-counting detector 2:

$$y = ax + b \quad (1)$$

where a is the change amount of the number y of detected photons with respect to the current value x and has a positive value, and b is the offset amount relating to noise in the photon-counting detector 2. The constants a and b are obtained, and the number y of detected photons is estimated at any current value x. The number y of detected photons obtained in the calibration of the CT apparatus is used as the number of received radiation photons in FIG. 5.

When the number of received photons exceeds a certain value, a difference occurs between the number of radiation photons received by the photon-counting detector 2 and the number of photons detected by the photon-counting detector 2. The photon-counting detector 2 counts the number of photons smaller than the actual number. The number of photons detected by the charge-integrating detector 3, thus, needs to be used for producing the projection data. The processing unit 34 calculates the number of photons used as a reference (hereinafter, described as a reference photon number) in accordance with the difference between the number of received radiation photons and the number of detected photons. The processing unit 34 determines which of the number of photons detected by photon-counting detector 2 or the charge-integrating detector 3 is used on the basis of the reference photon number.

Specifically, the processing unit 34 sets the reference photon number serving as a reference to determine which of the number of photons detected by photon-counting detector 2 or the charge-integrating detector 3 is used. The reference photon number is set when the CT apparatus 10 is calibrated. The number of received radiation photons is increased by means of the x-ray generator 12 of the CT apparatus 10. The processing unit 34 calculates a ratio of the number of detected photons to the number of received radiation photons in the photon-counting detector 2. The processing unit 34 sets, as the reference photon number, the number of detected photons that satisfies Expression (2):

$$0.8 \leq \frac{I_1}{I_0} < 1 \quad (2)$$

where $I_0$ is the number of radiation photons received by the photon-counting detector 2 and $I_1$ is the number of photons detected by the photon-counting detector 2.

A case where the number of radiation photons received by the photon-counting detector 2 and the number of photons detected by the photon-counting detector 2 are equal to each other corresponds to a case where the ratio in Expression (2) is 1. When the number of photons detected by the photon-counting detector 2 is used for producing the projection data, the ratio of the number of detected photons to the number of received radiation photons needs to be equal to or larger than 80% in order to grasp the radiation photons attenuated by the subject after passing through the subject. This case corresponds to a case where the ratio in expression (2) is 0.8. On the basis of Expression (2), when the ratio of the number of photons detected by the photon-counting detector 2 to the number of radiation photons received by the photon-counting detector 2 is equal to or larger than 0.8 and equal to or smaller than 1, the number of photons detected by the photon-counting detector is used for producing the projection data. On the basis of Expression (2), when the ratio of the number of photons detected by the photon-counting detector 2 to the number of radiation photons received by the photon-counting detector 2 is smaller than 0.8, the number of photons detected by the charge-integrating detector 3 is used for producing the projection data.

The photon-counting detector 2 can accurately detect the received radiation photons up to the number of received radiation photons of about 5 Mops, for example. When the number of received radiation photons is larger than about 5 Mcps, a difference occurs between the number of radiation photons received by the photon-counting detector 2 and the number of photons detected by the photon-counting detector 2. The number of photons detected by the photon-counting detector 2 is reduced. When the number of received photons is larger than about 5 Mops, the charge-integrating detector 3 accurately detects photons. When the number of detected photons in a case where the number of received photons is about 5 Mops is set as the reference photon number, the projection data is produced using the number of photons detected by the charge-integrating detector 3 in a case where the number of received photons is larger than about 5 Mcps. The reference photon number is preliminarily stored in a data table included in the first storage 35 of the image diagnosis apparatus 30.

Figure 6:
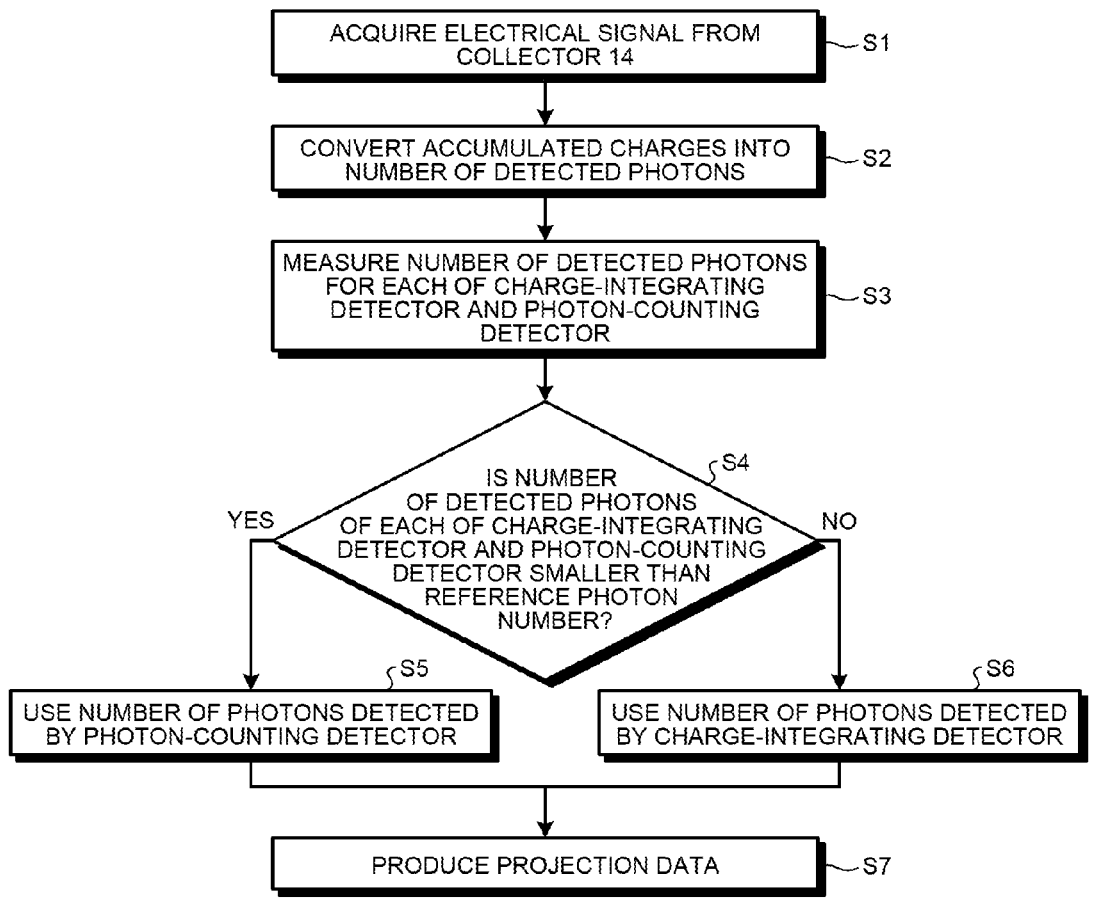
FIG. 6 is a flowchart explaining a processing procedure in a processing unit.

FIG. 6 illustrates a processing procedure performed by the processing unit 34 using Expression (2). The processing unit 34 acquires the electrical signal from the collector 14 (step S1). The processing unit 34 converts the charges accumulated in the capacitor 8 connected to the charge-integrating detector 3 into the number of detected photons (step S2). The processing unit 34 measures the number of detected photons for each of the photon-counting detector 2 and the charge-integrating detector 3 (step S3). The processing unit 34 determines whether the number of detected photons is smaller than the reference photon number for each of the photon-counting detector 2 and the charge-integrating detector 3 with reference to the reference photon number in the data table (step S4). If the number of detected photons of each of the photon-counting detector 2 and the charge-integrating detector 3 is smaller than the reference photon number, the processing unit 34 uses the number of photons detected by the photon-counting detector 2 (step S5). If the number of detected photons of each of the photon-counting detector 2 and the charge-integrating detector 3 is equal to or larger than the reference photon number, the processing unit 34 uses the number of photons detected by the charge-integrating detector 3 (step S6). The processing unit 34 produces the projection data using the number of photons detected by the photon-counting detector 2 or the charge-integrating detector 3 (step S7).

Figure 7:
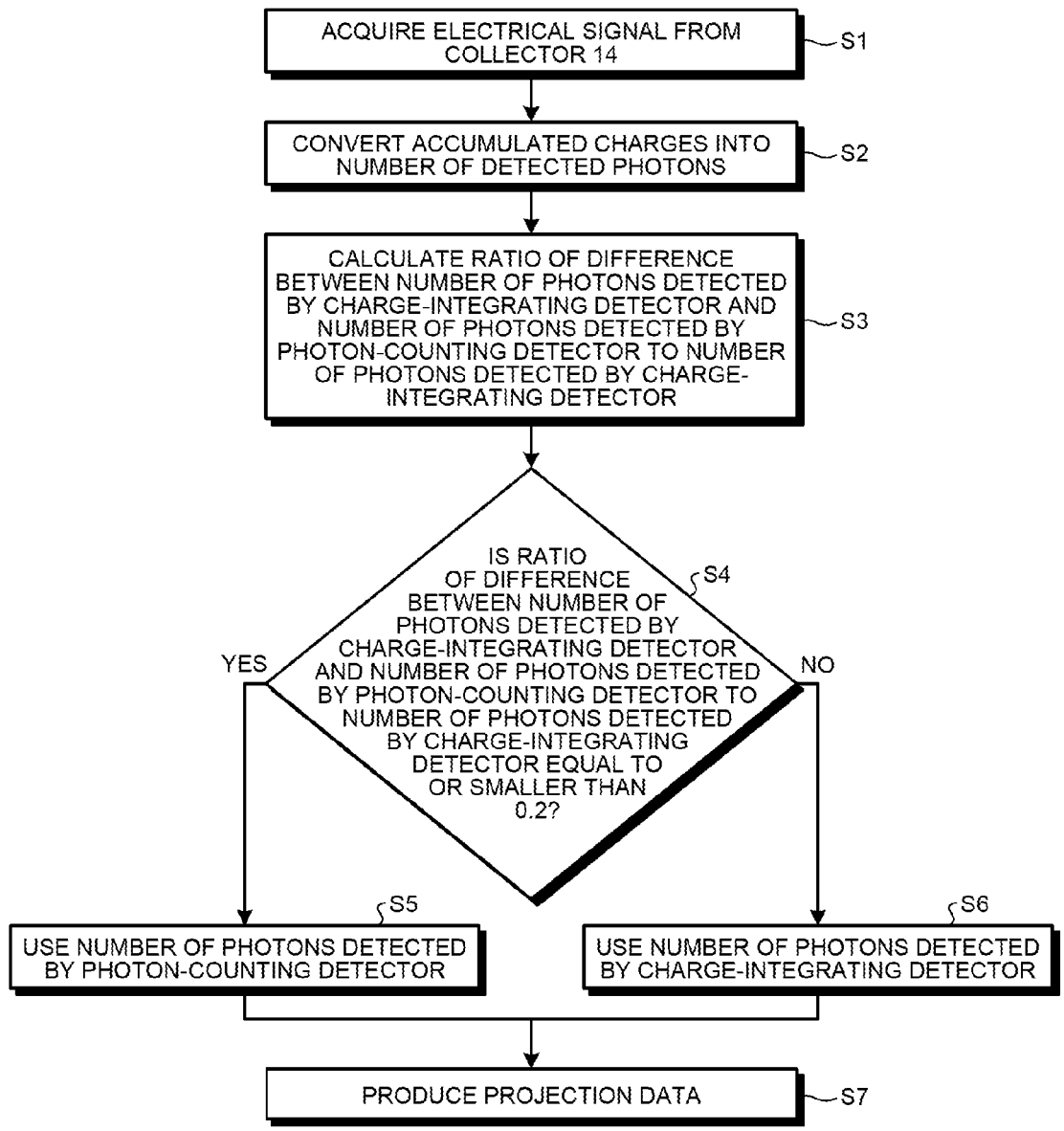
FIG. 7 is a flowchart explaining another processing procedure in the processing unit.

The following describes another method for producing the projection data with reference to the flowchart illustrated in FIG. 7. The processing unit 34 acquires the electrical signal from the collector 14 (step S1). The processing unit 34 converts the charges accumulated in the capacitor 8 connected to the charge-integrating detector 3 into the number of detected photons (step S2). The processing unit 34 calculates a ratio of the difference between the number of photons detected by the photon-counting detector 2 and the number of photons detected by the charge-integrating detector 3 to the number of photons detected by the charge-integrating detector 3 on the basis of Expression (3) (step S3), where $I_2$ is the number of photons detected by the charge-integrating detector 3.

$$\frac{|I_2 - I_1|}{I_2} \leq 0.2 \quad (3)$$

In FIG. 5, with an increase in the number $I_0$ of received radiation photons, the number $I_0$ of received radiation photons and the number $I_2$ of detected photons in the charge-integrating detector become nearly the same. Expression (2) is modified by approximating the number $I_0$ of received radiation photons by the number $I_2$ of detected photons in the charge-integrating detector 3. As a result, Expression (3) can be obtained. The processing unit 34 determines whether the ratio of the difference between the number of photons detected by the photon-counting detector 2 and the number of photons detected by the charge-integrating detector 3 to the number of photons detected by the charge-integrating detector 3 is equal to or smaller than 0.2 (step S4). If the ratio of the difference between the number of photons detected by the photon-counting detector 2 and the number of photons detected by the charge-integrating detector 3 to the number of photons detected by the charge-integrating detector 3 is equal to or smaller than 0.2, the processing unit 34 uses the number of photons detected by the photon-counting detector 2 (step S5). If the ratio of the difference between the number of photons detected by the photon-counting detector 2 and the number of photons detected by the charge-integrating detector 3 to the number of photons detected by the charge-integrating detector 3 is larger than 0.2, the processing unit 34 uses the number of photons detected by the charge-integrating detector 3 (step S6). The processing unit 34 produces the projection data using the number of photons detected by the photon-counting detector 2 or the charge-integrating detector 3 (step S7).

The detection device 1 can use the photon-counting detector 2 and the charge-integrating detector 3 simultaneously. As a result, it is unnecessary to switch the photon-counting detector 2 and the charge-integrating detector 3.

Figure 8:
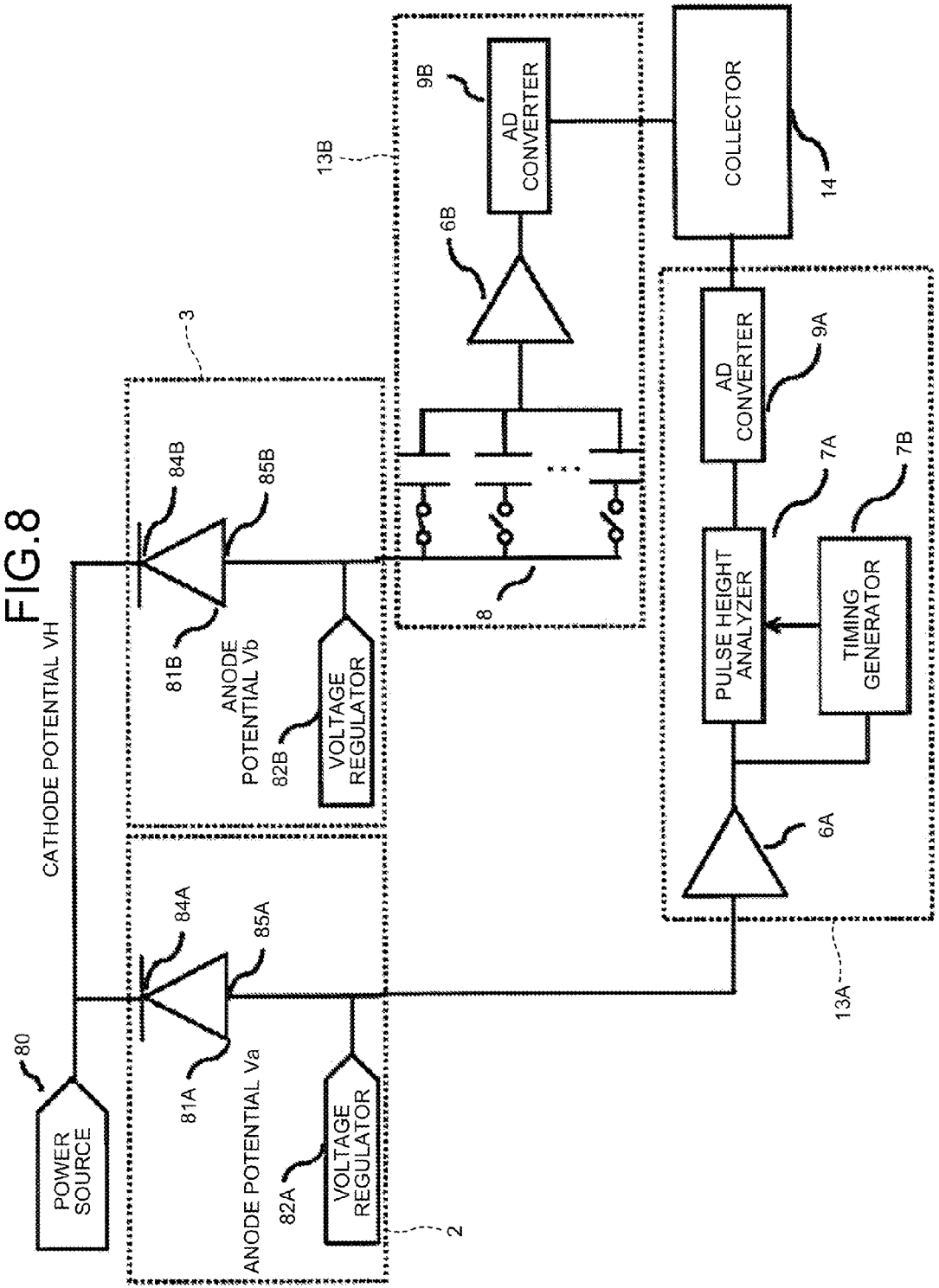
FIG. 8 is a schematic diagram illustrating circuit diagrams of the photon-counting detector and the charge-integrating detector.

FIG. 8 illustrates a structure of photodiodes included in the photon-counting detector 2 and the charge-integrating detector 3 arranged adjacent to each other. The photon-counting detector 2 includes a photodiode 81A while the charge-integrating detector 3 includes a photodiode 81B. The photodiode 81A includes a cathode 84A and an anode 85A. The photodiode 81B includes a cathode 84B and an anode 85B. To the cathode 84A of the photodiode 81A and the cathode 84B of the photodiode 81B, a power source 80 is connected. To the anode 85A of the photodiode 81A, a voltage regulator 82A is connected. To the anode 85B of the photodiode 81B, a voltage regulator 82B is connected.

The power source 80 applies a potential VH (V) to the cathode 84A of the photodiode 81A and the cathode 84B of the photodiode 81B. To the anode 85A of the photodiode 81A, a potential Va (V) is applied. To the anode 85B of the photodiode 81B, a potential Vb (V) is applied. The potential Va (V) applied to the anode 85A is regulated by the voltage regulator 82A while the potential Vb (V) applied to the anode 85B is regulated by the voltage regulator 82B. In the photodiode 81A, the potential Va (V) is applied to the anode 85A such that the potential Va (V) is smaller than the potential VH (V) applied to the cathode 84A. In the photodiode 81B, the potential Va (V) is applied to the anode 85B such that the potential Va (V) is smaller than the potential VH (V) applied to the cathode 84B. When a voltage applied between the cathode 84A and the anode 85A is increased in the photodiode 81A, a current rapidly starts to flow at a certain voltage. This voltage is defined as a threshold voltage Vbr (V). A mode in which the photodiode 81A is driven by applying a voltage equal to or larger than the threshold voltage Vbr (V) thereto is called a Geiger mode. When the photodiode 81A driven in the Geiger mode detects photons, the electrical signal is amplified. When radiation photons enter the radiation detector in which the photodiode 81A driven in the Geiger mode and the scintillator 4 are combined, the scintillator 4 generates scintillation photons in proportion to the energy of radiation photon and the photodiode 81A detects the scintillation photons, amplifies the electrical signal, and outputs the amplified electrical signal. As a result, the radiation detector can detect radiation photons as the pulse signal. The radiation detector thus structured functions as the photon-counting detector 2.

The photodiode 81B is driven by a voltage smaller than the threshold voltage Vbr (V). The photodiode 81B can detect a large number of photons and accumulates the electrical signal for a certain time in the capacitor 8. When radiation photons enter the radiation detector in which the photodiode 81B and the scintillator 4 are combined, the scintillator 4 generates scintillation photons in proportion to the energy of radiation photons and the photodiode 81B detects the scintillation photons, and outputs integration of generated electrical signals. As a result, a signal can be obtained that is proportional to the total amount of radiation photons entering the radiation detector per unit time. The radiation detector thus structured functions as the charge-integrating detector 3.

On the basis of relations among the threshold voltage Vbr (V), the cathode potential VH (V), the anode potential Va (V), and the anode potential Vb (V), the voltages applied to the photodiode 81A driven in the Geiger mode satisfy a relation of VH (V)–Va (V)>Vbr (V). The voltages applied to the photodiode 81B satisfy a relation of VH (V)–Vb (V)<Vbr (V).

The photon-counting detector 2 can output the amplified electrical signal. The photon-counting detector 2 is, thus, superior in detecting photons when an amount of radiation is small. The charge-integrating detector 3 can detects a large number of photons and accumulate the electrical signal for a certain time. The charge-integrating detector 3 is, thus, superior in detecting photons when an amount of radiation is large.

Figure 9:
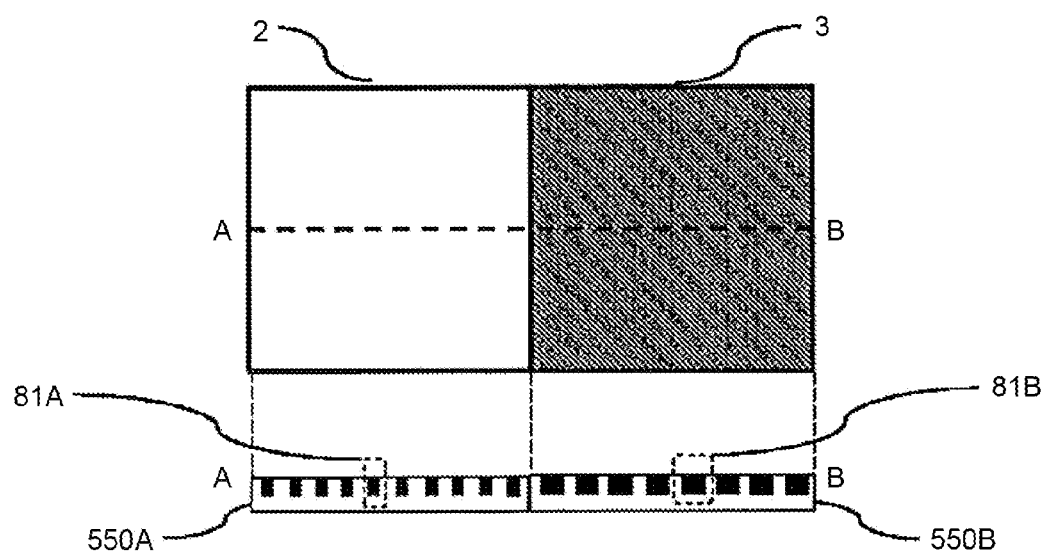
FIG. 9 is a cross-sectional view of the photon-counting detector and the charge-integrating detector.

FIG. 9 illustrates the photon-counting detector 2 and the charge-integrating detector 3 arranged adjacent to each other. On the upper side in FIG. 9, a view of the photon-counting detector 2 and the charge-integrating detector 3 is illustrated that is viewed from a detection surface side. On the lower side in FIG. 9, a cross-sectional view of the photon-counting detector 2 and the charge-integrating detector 3 is illustrated that is taken along the line AB of the view on the upper side in FIG. 9. The photodiodes 81A are arranged in a cross section 550A of the photon-counting detector 2. The photodiodes 81B are arranged in a cross section 550B of the charge-integrating detector 3. The photodiodes 81A and the photodiodes 81B are arranged in the channel direction and the slice direction. As illustrated in the cross-sectional view of FIG. 8, the area of a light receiving surface of the photodiode 81B is larger than that of the photodiode 81A. X-rays enter the detection device 1 without passing through the subject P in some cases. When x-rays enter the detection device 1 without passing through the subject P, the number of photons from the scintillator is increased. By increasing the area of the light receiving surface of each of the photodiodes 81b included in the charge-integrating detector 3, the detection efficiency of photons in the photodiodes 81B can be increased.

Figure 10:
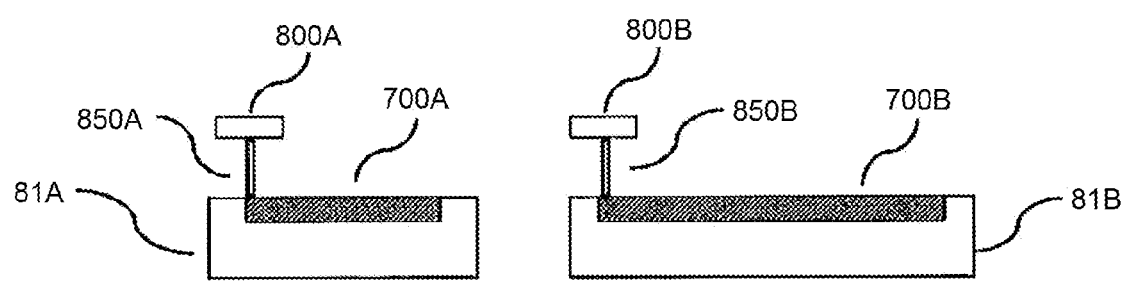
FIG. 10 is an enlarged view of photodiodes included in the photon-counting detector and the charge-integrating detector.

FIG. 10 illustrates enlarged views of the photodiodes 81A and 81B. The photodiode 81A includes a light receiving region 700A, an electrode 800A, and wiring 850A. The photodiode 81B includes a light receiving region 700B, an electrode 800B, and wiring 850B. The light receiving region 700A of the photodiode 81A can receive photons. The electrode 800A and the wiring 850A near the light receiving region 700A are regions where no photons can be received. The light receiving region 700B of the photodiode 81B can receive photons. The electrode 800B and the wiring 850B near the light receiving region 700B are regions where no photons can be received.

As illustrated in FIG. 10, the area of the light receiving region of the photodiode 81B is larger than that of the photodiode 81A. By increasing the area of the light receiving region of the photodiode 81B, the detection efficiency of photons can be increased. When the size of the photodiode 81B is increased, a ratio of the regions where no photons can be received, which are the electrode 800B and the wiring 850B, to the area of the surface receiving photons in the photodiode 81B is reduced. In addition, a ratio of the area of the light receiving region to the area of the surface receiving photons in the photodiode 81B is increased. Likewise, in the charge-integrating detector 3, a ratio of the area of the light receiving region to the area of the surface receiving photons is increased. As a result, the detection efficiency of photons is increased. For example, when the area of the light receiving region in the photodiode 81A is equal to or larger than 10 $\mu m^2$ and equal to or smaller than 25 $\mu m^2$, the area of the light receiving region in the photodiode 81B can be equal to or larger than 50 $\mu m^2$ and equal to or smaller than 500 $\mu m^2$.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A detection device comprising:
   a plurality of first detectors arranged on a two-dimensional plane, each first detector being configured to detect photons in a photon-counting manner;
   a plurality of second detectors arranged on the two-dimensional plane, each second detector being configured to detect photons in a charge-integrating manner; and
   a controller configured to perform control, using the number of photons detected by the second detector as a detection result when each of the number of photons detected by the first detector and the number of photons detected by the second detector is equal to or larger than a reference photon number, and using the number of photons detected by the first detector as the detection result when each of the number of photons detected by the first detector and the number of photons detected by the second detector is smaller than the reference photon number.

2. The device according to claim 1, wherein the first detectors and the second detectors are alternately arranged in a first direction on the two-dimensional plane.

3. The device according to claim 1, wherein the first detectors and the second detectors are alternately arranged in a first direction on the two-dimensional plane and in a second direction intersecting the first direction on the two-dimensional plane.

4. The device according to claim 1, wherein
the first detectors and the second detectors each include a photodiode, and
a light receiving surface of the photodiode of each second detector is larger than a light receiving surface of the photodiode of each first detector.

5. The device according to claim 4, wherein
the photodiode of each first detector operates by an applied voltage equal to or larger than a threshold voltage of the photodiode of the first detector, and
the photodiode of each second detector operates by an applied voltage smaller than a threshold voltage of the photodiode of the second detector.

6. The device according to claim 1, further comprising:
a circuit configured to detect an electrical signal output from the first detector; and
a capacitor configured to accumulate an electrical signal output from the second detector as charges.

7. A data processing method implemented by a computer connected to a detection device that includes a plurality of first detectors arranged on a two-dimensional plane, each first detector being configured to detect photons in a photon-counting manner and a plurality of second detectors arranged on the two-dimensional plane, each second detector being configured to detect photons in a charge-integrating manner, the method comprising:
performing control, using the number of photons detected by the second detector as a detection result when each of the number of photons detected by the first detector and the number of photons detected by the second detector is equal to or larger than a reference photon number, and using the number of photons detected by the first detector as the detection result when each of the number of photons detected by the first detector and the number of photons detected by the second detector is smaller than the reference photon number.

8. The method according to claim 7, wherein, at the performing of control, the number of photons detected by the first detector or the number of photons detected by the second detector is used as the detection result when the number of photons detected by the second detector is equal to or larger than the reference photon number and the number of photons detected by the first detector is equal to or smaller than the reference photon number.

9. A data processing method implemented by a computer connected to a detection device that includes a plurality of first detectors arranged on a two-dimensional plane, each first detector being configured to detect photons in a photon-counting manner and a plurality of second detectors arranged on the two-dimensional plane, each second detector being configured to detect photons in a charge-integrating manner, the method comprising:
performing control, using the number of photons detected by the first detector or the number of photons detected by the second detector as a detection result based on a ratio of a difference between the number of photons detected by the first detector and the number of photons detected by the second detector to the number of photons detected by the second detector.

* * * * *